United States Patent [19]

Cosens et al.

[11] 4,034,762
[45] July 12, 1977

[54] VAS CAUTERY APPARATUS

[75] Inventors: G. Ronald Cosens, Littleton; Richard J. Drew, Englewood, both of Colo.

[73] Assignee: Electro Medical Systems, Inc., Denver, Colo.

[21] Appl. No.: 601,793

[22] Filed: Aug. 4, 1975

[51] Int. Cl.² ........................................ A61B 17/36
[52] U.S. Cl. ..................... 128/303.17; 128/303.18; 219/234; 219/240
[58] Field of Search .......... 219/229, 230, 233, 234, 219/235, 238, 240, 242; 128/303.13, 303.17, 303.18, 303.19, 303.1, 404, 407, 408, 419 R, 421, 422, 423

[56] References Cited

U.S. PATENT DOCUMENTS

| | | | |
|---|---|---|---|
| 2,611,365 | 9/1952 | Rubens | 128/303.13 |
| 3,035,580 | 5/1962 | Guiorguiev | 128/303.18 |
| 3,518,996 | 7/1970 | Cortina | 128/422 |
| 3,799,168 | 3/1974 | Peters | 128/303.17 |
| 3,886,944 | 6/1975 | Jamshidi | 128/303.1 |
| 3,911,241 | 10/1975 | Jarrard | 128/303.17 |
| 3,911,930 | 10/1975 | Hagfors | 128/421 |
| 3,920,021 | 11/1975 | Hiltebrandt | 128/303.17 |

OTHER PUBLICATIONS

Schmidt et al., "Urology" vol. III, No. 5, May 1974, pp. 604 & 605.
Decker et al., "10th Annual Rocky Mtn. Bioengineering Symposium" Bolder Colorado, May 7-9, 1973, pp. 5-10.

Primary Examiner—William E. Kamm
Attorney, Agent, or Firm—Bruce G. Klaas

[57] ABSTRACT

This vas cautery apparatus includes a bipolar needle electrode, a pencil hand control, and a cautery electronic circuit. The bipolar needle electrode comprises a unitary center conductor and tip and the center conductor may be effectively insulated from an outer conductor by an insulating tubing. A relatively easily manipulated electrical connector joins the bipolar needle electrode to the pencil hand control. An output waveform from the cautery electronic circuit has an alternating potential characteristic during periods of the waveform.

7 Claims, 6 Drawing Figures

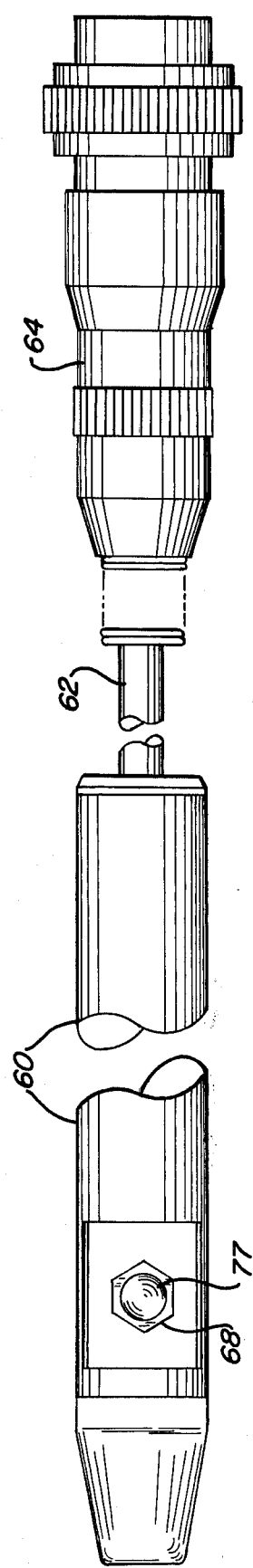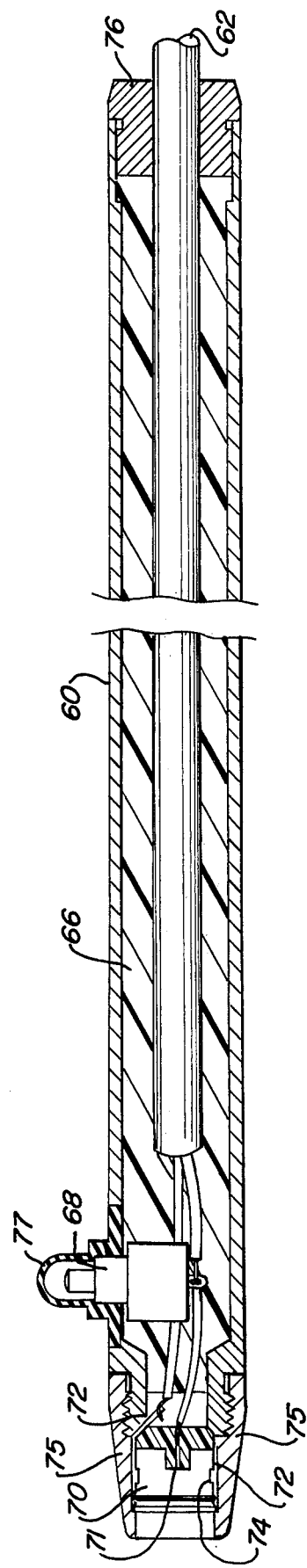

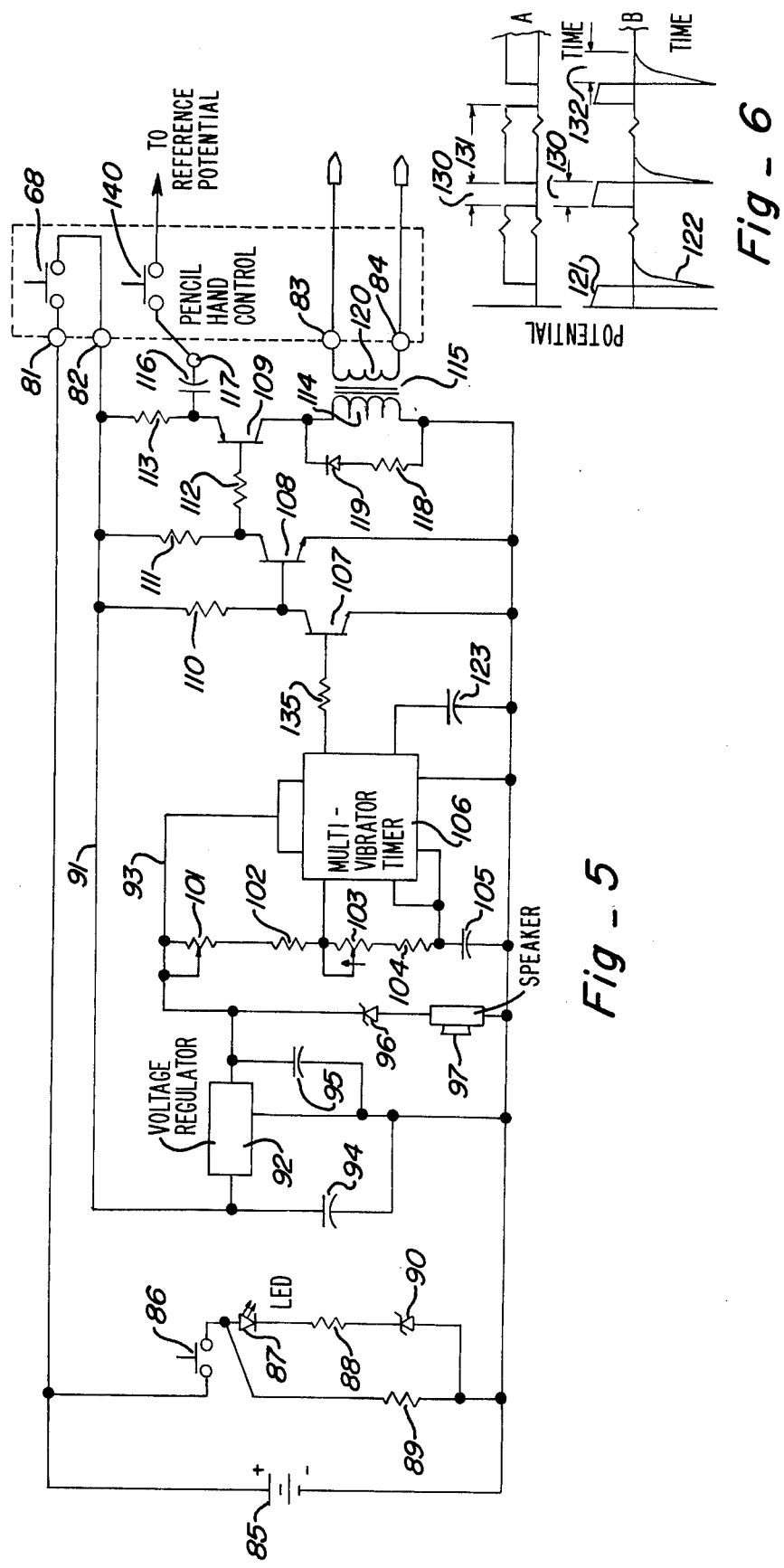

VAS CAUTERY APPARATUS

BACKGROUND AND SUMMARY OF THE INVENTION

This invention relates to electrical apparatus for electrocauterization of living tissue in a surgical procedure, and more specifically, to such apparatus particularly useful for sealing the lumen of a vas or other tubular vessel, for example the vas deferens during a vasectomy operation. Vasectomy operations, of course, are well-known and serve the purposes of allowing an effective method of birth control by males and of limiting population growth.

Vasectomy operations are typically purely surgical procedures involving incision, transection of each of the two vasa deferens, tying or otherwise blocking each of the four lumina or severed ends of the vasa, misaligning the two severed ends of each of the two severed vasa, and closing the incision. These conventional techniques have had less than the desired success due to such factors as the ends of the vasa not correctly sealing and thereby causing spermatic granuloma, or the reestablishment of the duct passages. The typical failure rates in vasectomies, for one cause or another, has been estimated at 2 to 6 percent. This failure rate is relatively high and developments which reduce the rate are certainly important.

Equally desirable as the vasectomy itself is the ability to render the vasectomy operation reversible, that is, to allow the rejoinder of the previously severed vas through another surgical operation to once again cause the male to be fertile. Reversibility may become more important as the key factor to a wider acceptance and thus a higher incidence of vasectomies. The reversibility of vasectomies performed by conventional surgical techniques is extremely low. Typical reversibility techniques would involve surgery, excision of the sealed ends of the vas, stretching and aligning the now open ends of the vas, and retaining the vas in alignment so that healing to rejoin the vasa may occur. Apparently, tying the severed ends during conventional vasectomy operations induces significant trauma in the severed ends of the vas and requires excision of large amounts of the sealed vas and considerable stretching to realign the vas, all of which deters the proper healing. Another possible contributing cause which may reduce the success rate in reversing the vasectomy may be sperm antibody production. It has been discovered that in most conventional vasectomy operations significant amounts of sperm antibodies are generally present subsequent to the operation. The relationship between the reversal failures and the sperm antibodies is not certainly determined, but the presence of the sperm antibodies is suspected a contributing cause to the failure. Conventional vasectomy techniques have shown a marked proclivity for sperm antibody production, and to eliminate undue sperm antibody production may be to significantly increase the success rate of operation to reverse vasectomies.

It has recently been determined that electrocauterization of the lumen of the transected vas provides significant advantages over the conventional techniques in vasectomy operations. Electrocauterization virtually eliminates failures. Electrocauterization is a much faster procedure allowing a more rapid reclosure of the incision without the prolonged and sometimes difficult procedure of tying or otherwise blocking the transected vas. Furthermore the electrocauterization technique has shown a marked decrease if not elimination of the production of sperm antibodies subsequent to the operation. It has been determined that original electrocauterization of the transected vas has caused a higher rate of subsequent successful operations to rejoin the previously severed vasa. The operation to reverse the vasectomy is performed in the conventional manner, but apparently the electrocauterization of the lumen of the transected vasa in the original operation is the primary factor in determining the greater success in the operation to reverse the vasectomy.

At the time of original efforts to apply electrocauterization techniques to vasectomies, existing electrocautery apparatus was inappropriate due to the high power output supplied and the availability of only a conventional needle electrode and diffuse electrode or patient plate with which to apply the electrical energy during the electrocautery process. Furthermore known electrocautery apparatus was not portable due to the power requirements which normally require the use of conventional AC sources. Thus to effectively evaluate electrocauterization techniques in vasectomies, special vas cautery apparatus for such use was developed. Such apparatus was described in "An Electrocautery Instrument for the Fulguration of the Vas Deferens during Vasectomy for Sterilization", Proc. 10th *Annual Rocky Mountain Bio-Engineering Symposium*, 1973, pages 5–10 and in "*Vas Cautery: Battery Powered Instrument for Vasectomy*", in *Urology*, May 1964, page 604–605. The present invention defines significant improvements over the individual components of the known vas cautery apparatus, and thus provides a significantly more useable, reliable, and success-producing apparatus.

One of the principle deficiencies in known vas cautery apparatus involves the electrode used to apply the electrical energy during the cauterization. This electrode, known as a needle electrode, is bipolar, meaning there are two active electrodes between which the electrical energy flows to cause the cauterization. The bipolar needle electrodes originally used for vas cauterization were designed for other uses such as deep brain encephalographic recording and had to be considerably modified. Later versions of these needle electrode involved the use of hypodermic needles in which a center conductor and epoxy dielectric insulation were inserted through the internal bore of the hypodermic needle and a tip was soldered to the end of the center conductor. This version was more successful than the encephalographic electrode but was subject to many problems, particularly those relating to durability, strength and ease of production. Insulation of the conductors leading to the two active electrodes posed a considerable problem in the prior art. Generally the insulation consisted of epoxy dielectric material and such material was prone to break down and crumble due to the high temperatures during the cauterization process or during sterilization in an autoclave. The epoxy lacked the strength to adequately support the center conductor and was awkward to apply since the components were typically dipped in the epoxy and certain electrodes were exposed by scraping the epoxy after hardening. The soldered tip of the center conductor was prone to come loose and possibly fall off, which of course could create obviously serious consequences during an operation. The electrical connector for supplying power to the bipolar needle electrode was weak, and after limited repeated use was considerably weakened since the electrode pencil must be detached and sterilized after each operation. The prior art has counseled that solutions to many of these problems may be obtained by increasing the thickness of the dielectric epoxy adhesive. However, this solution is unacceptable since the overall outside thickness of the bipolar needle electrode would be increased thereby provoking problems during the insertion and use of the bipolar needle electrode in the transected vas. It is also questionable whether increased epoxy would solve the problems relating to breakdown of the insulation.

The known vas cautery electronic circuits provide a generally square pulse wave output of a positive polarity having the desired voltage amplitude, power and duty cycle characteristics. This arrangement has proved reasonably satisfactory, but certain disadvantages, deficiencies and areas for improvement are nevertheless present. The single polarity pulse output wave requires higher than necessary amounts of power from the battery to deliver the requisite energy for electrocauterization, which of course tends to decrease battery life, reduce the expected number of operations which may be performed, and slightly prolong the operative procedure since more output pulses are required to deliver sufficient energy. Typical experiences in analogous arts have shown that the single polarity pulse output wave may have a significant tendency to cause the degradation of the active electrodes of the bipolar needle electrode. The single polarity current usually causes an electrolysis-like action in depositing ions on the active electrodes. The prior art electronic cautery circuits have also generally failed to deliver consistent and repeatable output pulse waves, especially from the battery power supplies, which made consistency in operative results hard to obtain.

Known vas cautery apparatus further include a pencil hand control to which the bipolar needle electrode is connected and through which the pulse wave output is supplied to the bipolar needle electrode. A problem resulting from this arrangement is that the prior art electrical connector interfacing the pencil hand control to the bipolar needle electrode requires undue force in mating and separation, thereby decreasing the durability and lifetime of the bipolar needle electrode. Furthermore the materials from which the prior art pencil hand controls were made were not susceptible to withstanding repeated sterilization processes and were subject to deterioration or destruction at high temperatures or in other sterilization environments.

In view of the worthwhile objectives of vas cautery apparatus, it is a general object of this invention to provide an improved apparatus which may secure wider and more successful acceptance of vasectomies and enhance the success rate of vasectomies through vas electrocauterization.

It is an object of this invention to provide a very reliable and consistently operating vas cautery apparatus which may be relatively easily manufactured to thereby increase the distribution, use and availability of such apparatus.

It is another object of this invention to provide significant improvements to the durability, strength and design arrangement of known bipolar needle electrodes used in vas cautery apparatus.

It is another object of this invention to provide a new bipolar needle electrode for vas cautery apparatus which is of reduced cost and easily manufactured in large quantities to encourage the use of bipolar needle electrodes in situations where subsequent sterilization is not possible, since disposal of used bipolar needle electrodes of reduced cost and ready availability will not be prohibitive.

It is a further object of this invention to provide an improved vas cautery electrical circuit which delivers a unique waveform output to thereby increase battery life, increase power output and prevent degradation of the active electrodes of the bipolar needle electrode used in conjunction with the circuitry.

It is a further object of this invention to provide an improved electronic circuit for vas cautery apparatus which provides uniformly consistent output wave characteristics to thereby invoke more successful cauterization results.

It is still a further object of this invention to provide an improved cautery pencil device for a vas cautery apparatus which may be readily sterilized without destruction and which promotes increased durability of the bipolar needle electrode.

To secure these and other objects, the present invention provides improvements in individual components and to the vas cautery apparatus itself, encompassing improvements to the bipolar needle electrode, the cautery pencil and the cautery electronic circuitry. The improved bipolar needle electrode comprises individually manufactured parts, including a unitary center conductor and tip, with the tip forming one active electrode, a tubular outside conductor forming another active electrode and being separated from the center conductor by an insulating tubing, and insulation tubing surrounding the outer conductor except the exposed active electrode. This assembly is attached rigidly to a conventional push-pull electrical connector and a handle or grip is provided to easily insert and remove the bipolar needle electrode from its mating push-pull connector. The improved pencil hand control is comprised of plastic materials capable of withstanding the environments of all ordinary sterilization techniques, and specifically, includes the mating portion of the electrical push-pull connector of the bipolar needle electrode thereby allowing ready detachment. The improved vas cautery electronic circuit includes a voltage regulator to supply a consistant voltage reference level even as the battery degrades through use, and the output waveform provided has an alternating potential characteristic during periods of the waveform which increases power output and battery life and prolongs the life of the bipolar needle electrode.

The invention, as to its organization and method of operation and practice, together with further objects and advantages, will best be understood by reference to the following brief description of the drawings and detailed description of the invention.

BRIEF DESCRIPTION OF THE DRAWINGS

FIG. 3 is a broken perspective view of a portion of one embodiment of a pencil hand control which comprises a portion of the present invention;

FIG. 4 is a vertical section of one portion of one embodiment of the pencil hand control of FIG. 3;

FIG. 5 is a schematic diagram of one embodiment of a vas cautery electronic circuit employed in the present invention; and FIG. 6, lines A and B are waveforms illustrating the operation of the vas cautery electronic circuit of FIG. 5.

DETAILED DESCRIPTION OF THE INVENTION

Figure 1:
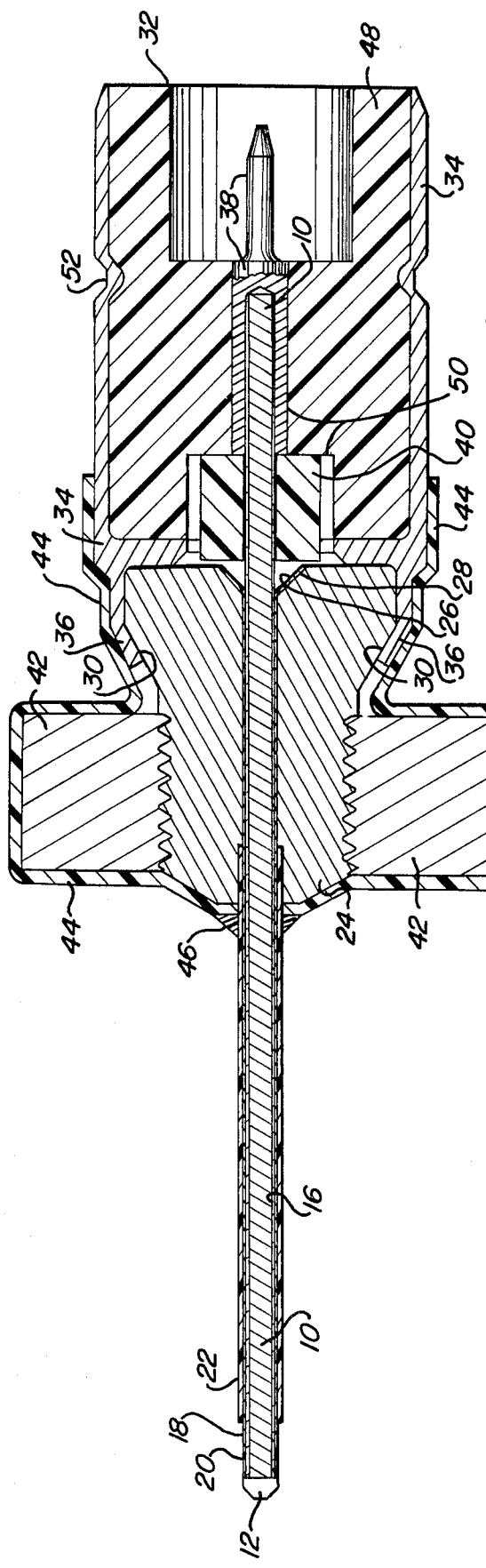
FIG. 1 is a vertical section of one embodiment of a bipolar needle electrode which comprises a portion of the present invention.

Referring now to FIG. 1 an improved bipolar needle electrode is illustrated. It includes an axially extending center conductor 10 terminating at a tip 12. The center conductor 10 and tip 12 are integrally formed preferably from a unitary piece of machined metal such as stainless steel, which has good electrical conductive properties and has the ability to withstand repeated introductions into the environments of ordinary sterilization processes. The tip 12 might be attached to the center conductor 10 by a rigid mechanical such as with threads, but such a connection must make tip unitary with respect to the center conductor. As can best be seen in FIG. 2 the center conductor 10 and tip 12 are circular and the tip 12 is formed by an annular shoulder 14 extending radially out from the center conductor to provide a desirable outside diameter 12 of approximately 0.030 inch. The tip, including an axially-extending surface or portion 15 parallel to the center conductor forms one active electrode of the bipolar needle electrode. The tip is tapered or rounded from portion 15 to facilitate its insertion into the transected vas. An inner portion of electrical insulating material, which in one embodiment comprises an electrically insulating tubing 16, fits concentrically over the center conductor and preferably extends along the length of the center conductor 10. The insulating tubing 16 should have high dielectric strength and be relatively immune to sterilization environments. A polymide tubing called micro "ML" manufactured by Niemand Bros., Inc., has been found satisfactory.

An outer elongated tubular conductor 18, also preferably of stainless steel, fits concentrically with and extends axially along the inner insulating tubing 16. A terminal end portion 17 of conductor 18 includes a radially extending shoulder portion 19. The outer tubular conductor 18 has approximately the same outside diameter as the tip 12, and the shoulder portion 19 is axially displaced from the shoulder 14 of the tip 12. An epoxy adhesive 20 of dielectric material is inserted in the space between the shoulder portion 19 of outer electrode 18 and the shoulder 14 of tip 12 to form a smooth surface of relatively uniform outside diameter from the tip 12 to and including and exposed portion of the outer tubular conductor 18. In conjunction with the inner insulating tubing, the epoxy adhesive 20 electrically insulates the center conductor 10 and tip 12 from the outer tubular conductor 18. An outer insulating tubing 22 having characteristics similar to those of the inner tubing 16 may be applied concentrically over the outer tubular conductor 18. A predetermined amount of the outer tubular conductor is left exposed, and the exposed portion of the outer tubular conductor at the terminal end portion 17 forms the other active electrode. Thus the bipolar needle electrode includes two active electrodes, one formed by the tip 12 with portion 15 and the other formed by the exposed terminal end portion of the outer conductor 18.

To accomplish electrocauterization, after the vas has been transected, the bipolar needle electrode is inserted into the lumen of the vas up to and possibly slightly lapping over the outer insulating tubing 22. Electrical energy is conducted respectively to the two active electrodes and flows between these electrodes through the epithelial lining of the vas surrounding the vas musculature. Initially the epithelial lining provides a very low impedance path for the flow of electrical energy but the impedance increases as the epithelial lining is destroyed, leaving the surrounding muscle cells virtually unaffected. The epithelial cells slough off and the exposed muscle tissue is available to produce scar tissue which seals the vas.

Apparently the exposed muscle tissue will heal forming a more secure blockage for the vas, and this natural healing of the exposed muscle tissue evidently promotes a better proclivity for success in reversing the operation. The more natural healing evidently also is significant in reducing or eliminating sperm antibody protection. The unitary center electrode and tip offer considerably increased strength and durability over the prior art's flexible center conductor with a soldered-on tip. In the present invention, the unitary center electrode and tip actually provide support for the construction of the bipolar needle electrode unlike the prior art where the outer conductor provided the most significant support. The inner insulating tubing is far superior over the prior art epoxy in qualities of electrical insulation and of resistance to sterilization environments which promote a longer useable lifetime for the bipolar needle electrode.

In FIG. 1, the end of the bipolar needle electrode opposite of the tip 12 is substantially connected to one portion of a conventional electrical connector of the push-pull mating type. The push-pull electrical connector allows easy insertion and release of the bipolar needle electrode without causing undue force or strain on its various elements. An electrode collar 24 fits concentrically with the outer tubular conductor 18 and provides an electrical conduction path therebetween and provides strength and support. The electrode collar 24 has good electrical conductive properties, and may be made of brass. The outer tubular conductor 18 includes a flared end 26 which is received in a flared receptacle 28 to provide a good electrical conductive path. The electrode collar 24 includes an annular conical concentric sloping portion 30. The electrode collar 24 is retained adjacent one mating portion of an electrical connector 32 having an outside electrically conducting housing 34 by crimping or bending extensions 36 from housing 34 onto the sloping portion 30 of the electrode collar 24. By so doing a firm mechanical and electrical connection is provided between the electrode collar and the housing of the mating portion of the electrical connector 32. A conductive male contact pin 38 may be soldered to the center conductor 10, and a mechanical spacer 40 of plastic material such as Delrin separates and retains male contact pin 38 from the electrode collar 24. The contact pin 38 and the spacer 40 both fit within an opening 50 provided in electrical insulation 48 such as Teflon in the interior of the mating portion of the electrical connector 32. A concentric indention 52 in the housing 34 is a means for holding the two mating portions of the electrical connector together.

A nut 42, preferably round, is threaded onto a portion of the electrode collar 24 and functionally serves as a means for gripping the bipolar needle electrode to easily handle it especially during push-pull attachment and detachment at the electrical connector. A piece of heat shrink tubing 44 is firmly shrunk over portions of the electrode collar 24, the round nut 42, and the housing 34 of the electrical connector 32, thus electrically insulating that portion of the bipolar needle electrode that would otherwise be exposed when inserted in the pencil hand control. Epoxy retainer 46 firmly retains the outer insulating tubing 22 to the heat shrink tubing 44.

The procedure in assembling the bipolar needle electrode is that the inner insulating tubing 16 is inserted over the center conductor 10. The outer tubular conductor 18 is inserted in the bore of the electrode collar 24 and the flared end 26 is soldered to the flared receptacle 28. The center conductor 10 and tip 12 with the inner insulating tubing 16 are inserted through the interior bore of the outer tubular conductor 18. The spacer 40 is inserted over the center conductor and inner insulating tubing, and the male contact pin 38 is soldered to the center conductor 10. The electrical connector 32 is slipped over and the extensions 36 are crimped to the electrode collar 24 thus firmly attaching the portion of the connector 32 as a part of the bipolar needle electrode. The round nut 42 is screwed on the electrode collar 24 and the outer insulating tubing 22 is inserted over the outer conductor 18 and slightly into a receptacle formed in the electrode collar. The heat shrink tubing 44 is then firmly heat attached, and epoxy adhesive 20 and epoxy retainer 46 are applied.

From the foregoing description of the elements, the procedure of assembly and the described advantages, it can readily be seen that the bipolar needle electrode comprised of individually manufactured components is easily susceptible for mass production. The interconnection of the preformed elements allows the bipolar needle electrode to be manufactured at significantly less cost than the prior art bipolar needle electrodes. Furthermore, the elements and assembly of the elements allows for precise dimensional tolerances and consistently similar characteristics from one bipolar needle electrode to another. These factors, of course, increase the chance of consistently successful operative results. The relatively rugged construction provides a more durable product, and the relatively easy manipulated push-pull electrical connector avoids undue stress to the various elements. The handle allows easier handling of the bipolar needle electrode.

Figure 2:
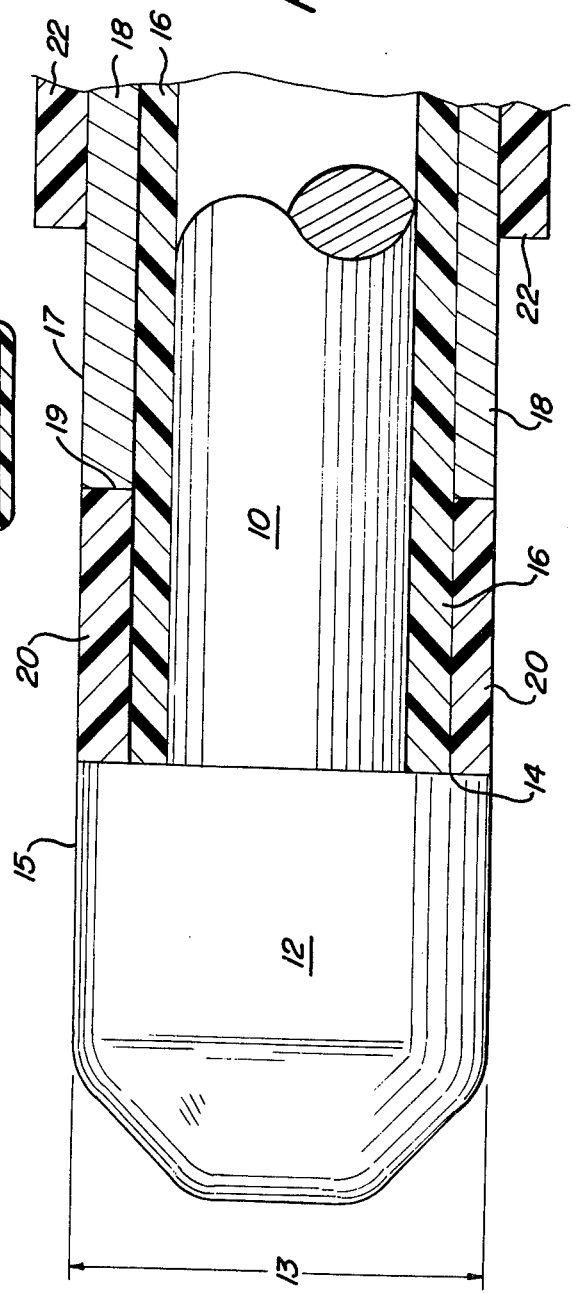
FIG. 2 is an enlarged cross-section of a portion of FIG. 1.

The bipolar needle previously described in FIGS. 1 and 2 may be selectively mechanically and electrically attached to a pencil hand control as shown in FIGS. 3 and 4. The pencil hand control includes a body 60 for receiving the bipolar needle electrode. The body 60 is of a size so that the use of the bipolar needle electrode during the cautery process is easily controlled. An electrical connecting cable 62 and an electrical connector 64 supply electrical energy. As shown more specifically in FIG. 4, the body of 60 may have a main hollow center section 66 for receiving a push button electrical switch 68 in the side of the center section 66. A mating portion 70 of the electrical connector of the bipolar needle electrode is retained adjacent the main center section 66 by a nose piece 75 which may be threaded on to main center section 66. The electrical cable 62 extends through a rear closure 76 which may be threaded on to the center section 66. The cable 62 includes four insulated conductors, two of which are respectively attached to a center socket 71 and an outer housing 72 of the mating portion 70 of the electrical connector. A concentric ring 74 is adapted to fit within the concentric indention 52 of the connectors 32 of the bipolar needle electrode. The other two conductors are connected to the push button switch 68 to conduct, when switch 68 is operated, electrical current for activating the cautery electronic circuit described more fully subsequently. A flexible boot 77 or cover for the switch 68 is provided to isolate and protect the switch from intrusion by environmental elements, such as moisture. To operate the switch the boot cover 77 is merely depressed to contact the button associated with the switch 68.

All of the materials of pencil hand control have ability to withstand all usual and normal forms of sterilization without degrading. The electrical connectors 64 and 70 have metallic and insulating components. The electrical cable 62 has an outer sheath of silicon rubber insulation which covers jackets of silicone rubber insulation over each of the individual four conductors within the cable 62. The center section 66, the nose piece 75 and the rear closure 76 may be made of plastic material such as Delrin which has the properties of machineability and high strength, yet will withstand the temperatures and chemicals of various techniques of sterilization.

A circuit for supplying electrical power as a unique output waveform is shown schematically in FIG. 5. The circuitry in FIG. 5 may be enclosed in a suitable mechanical closure with an electrical connector provided for mating with the electrical connector 64 of the pencil hand control. An electrical connection is shown schematically at terminals 81 through 84. Terminals 83 and 84 in conjunction with the circuit provide a means for supplying the output waveform to the two active electrodes of the bipolar needle electrode. Terminals 81 and 82 are connected through the cable 62 to the electrical switch 68 of the pencil hand control. When switch 68 is closed, the circuit of FIG. 5 is provided with electrical power from a supply such as battery 85. Battery 85 may be contained within mechanical closure housing the circuitry of FIG. 5 and allows the vas cautery apparatus to be portable and useable in remote and undeveloped areas. A battery test circuit comprises switch 86, light emitting diode (LED) 87, resistors 88 and 89 and zener diode 90. Zener diode 90 in series with resistor 88 and LED 87 is a voltage reference by which to compare the output battery voltage. Resistor 89 simulates a load on the battery, and allows the battery voltage to be determined under a simulated-use condition. When switch 86 is depressed, if the output voltage of battery 85 is unacceptably low as compared to the voltage across zener diode 90 and the resistor 88, the LED 87 will not light, indicating that the battery 85 needs to be replaced. Of course the switch 86 and the LED 87 may be accessibly mounted at the exterior of the mechanical closure.

To initiate use, operation of switch 68 applies battery voltage on conductor 91 to the input of a voltage regulator 92. The output of the voltage regulator 92 on conductor 93 is substantially regulated to potential less than that of the battery 85 and forms a reference for deriving precise output waveform characteristics. Capacitors 94 and 95 are filter capacitors for the voltage regulator 92. When voltage is present on conductor 93, as a result of the closure switch 68, zener diode 96 in series with a speaker device 97 conducts current. The zener diode 96 merely reduces the supply of voltage to speaker 97. The audio signal supplied by device 97 indicates to the surgeon that electrical energy is available for cauterization. Resistors 101 through 104 and capacitor 105 form two RC time constant circuits for input to a multivibrator 106, such as Signetics Timer 555. The output of the multivibrator 106 is a square wave as shown in FIG. 6, line A, whose pulse width duration and pulse repetition rate are determined by the two time constants of the RC network elements 101 through 105. Adjustable resistor 103 and resistor 104 in conjunction with capacitor 105 determine the pulse width. Resistors 101 through 104 and capacitor 105 determine the pulse repetition rate. A typical square wave output from the multivibrator 106 is shown in FIG. 6, Line A. Here the "off"time, referenced 130, is ideally 60 microseconds but is adjustable approximately plus or minus 20%. The "on" time typically is 1291 microseconds, shown by a broken time scale and referenced 131. This makes one period of the square wave approximately 1351 microseconds giving a pulse repetition rate of about 740 pulses per second. The pulse repetition rate may be adjustable approximately in the range of 740 pulses per second pulse or minus 20%.

Amplification and inversion of the square wave multivibrator output of FIG. 6, line A is by a transistor 107 biased by the output of the multivibrator through resistor 135, and transistors 108 and 109 amplify the inverted square wave. Resistors 110, 111, 112 and 113 bias the transistors 107, 108 and 109 accordingly. Transistor 109 functions primarily as a current switch for driving current to a primary winding 114 of a transformer 115. Capacitor 116 is connected to the emitter of transistor 109 and is a storage capacitor for current which transistor 109 directs to the primary winding 114. Capacitor 116 also serves as a bypass capacitor to maintain the current gain through the primary winding 114 at high pulse repetition rates. Terminal 117 must be connected to reference potential as by switch 140 to make capacitor 116 operable if these advantages are desired.

A resistor 118 in series with a diode 119 is connected in parallel with the primary winding 114 of transformer 115. Diode 119 is reverse biased to block current flow through resistor 118 when transistor 109 is switched on, thus allowing the transformer to deliver a pulse to output terminals 83 and 84 through the secondary winding 120 of the transformer. At the termination of the pulse switched by transistor 109, the inductive properties of primary winding 114 induces a decaying current flow which causes diode 119 to become forward biased. The decaying current circulates through resistor 118, diode 119 and the primary winding 114, and the impedance of resistor 118 causes the voltage input signal to transformer 115 of the opposite polarity to that supplied by the transistor 109. The opposite polarity signal induces a spike of voltage of opposite polarity to that of the pulse output at terminals 83 and 84, and the voltage spike generally decays rapidly as the current through resistor 118 decays. FIG. 6, line B shows a typical output waveform at terminals 83 and 84 having the alternating characteristic as just described. The output pulse, typically positive, is indicated at 121, and the spike, typically negative, is indicated at 122.

According to one embodiment of the invention one positive pulse and one negative spike are provided during each period of the output waveform as shown in FIG. 6, line B. The width of pulse 121 corresponds to the "off" time in FIG. 6, line A, and is typically 60 microseconds plus or minus 20% due to the adjustability of resistors 101 and 103 in the RC network of the multivibrator, as previously described. Likewise, the output waveform repetition rate is variable. It has been determined that an output potential of pulse 121 suitable for performing vasectomy operations may fall in the range of 200 to 240 volts. Typically the voltage of the pulse degrades or decreases during the width of the pulse due to the characteristics of the resistor 113, the capacitor 116, the transformer 115 and the impedance of the vas tissue. The absolute value of the peak potential of the spike 122 has been observed as satisfactory at approximately 420 volts. This voltage decreases very rapidly and generally decays to approximately zero in 80-100 microseconds, referenced 132 in FIG. 6, line B.

A significant factor of the output waveform is the alternating polarity characteristic during each period of the waveform as shown in FIG. 6, line B. This characteristic is expected to significantly prolong the life of the active electrodes of the bipolar needle electrode by reversing current flow between the two electrodes during each period of the output waveform. The reversing current inhibits electrolysis-like deposition of ions on the active electrodes, since the reversing current carries ions in both directions during each period of the waveform between the active electrodes. Furthermore the spike of opposite polarity adds extra power to the output waveform, thus allowing cauterization to be completed more quickly with the use of less power from battery 85. The life of the battery 85 is prolonged and increased usefulness resuls, which is particularly important in remote, isolated and undeveloped areas. The voltage supplies a precise reference for fine resolution of the pulse width and the pulse repetition rate of the output wave supplied. Such resolution is particularly important to secure uniform operative results when using the vas cautery apparatus.

The characteristics output waveform delivered to the vas during electrocauterization depends upon the impedance of the vas. During the initial application of the output wave and before any significant electrocauterization has occured the impedance of the vas is low. The low impedance causes the output waveform of FIG. 6, line B to initially have significantly decreased voltage. For example the positive pulse 121 may be of only 75 to 80 volts, and the negative spike may be reduced greatly. As the electrocauterization continues as the output wave is applied, the voltage increases as the impedance increases due to cauterization. Typically the initial impedance of the lumen is about 250 ohms, but when this is reflected into the primary winding of the transformer it has the effect of significantly lower impedance which causes the described reduced output waveform. It should also be recognized that the pulse 121 is merely a general representation of the output waveform, and in some situations it may be impossible to secure, for example, the instantaneous rise times and abrupt corners illustrated in FIG. 6, line B.

In operation, the bipolar needle electrode of FIGS. 1 and 2 is connected through the push-pull electrical connector to the pencil hand control of FIGS. 3 and 4. The pencil hand control is connected to the cautery circuitry of FIG. 5 at terminals 81 through 84. The surgeon then checks the battery by depressing switch 86. If LED 87 provides a light signal the battery has sufficient energy to conduct a vasectomy operation. When the vas has been transected, the bipolar needle electrode is inserted into the lumen of the vas and switch 68 is depressed which causes the electrical circuitry of FIG. 5 to become operative. The square wave output from ultivibrator 106 is inverted and amplified and current representative of the square wave is delivered to the transformer 115. The output waveform of FIG. 6B supplied to terminals 83 and 84 is delivered to the active electrodes of the bipolar needle electrode in the lumen. The surgeon holds switch 68 depressed long enough to accomplish the electrocauterization and then removes the bipolar needle electrode and releases switch 68. The pencil hand control allows the physician to control the placement of the bipolar needle electrode and to selectively energize its active electrodes quickly and with only one hand.

One embodiment of the invention has been shown and described with particularity, and it is probable that those skilled in the art will perceive changes and modifications without departing from the scope of the invention. Therefore it is intended by the appended claims to cover all such changes and modifications as fall within the true spirit and scope of the invention.

The invention claimed is:

1. An electrical apparatus for supplying an electrical energy waveform for use by an electrode device to effect electrocauterization of a transected vas, comprising:
   battery means for providing a supply of electrical power for said apparatus;
   means for providing source of substantially regulated potential from the battery power supply means;
   means connected to the regulated potential source means for producing a square wave having predetermined pulse width and pulse repetition rate; and
   means utilizing the square wave for supplying an output waveform of a pulse of one polarity having a maximum absolute potential followed by a spike of opposite polarity having an absolute potential greater than the maximum absolute potential of the pulse to increase utilization of the power supplied by the battery means.

2. An electrical apparatus as recited in claim 1 wherein the output waveform supplied includes a pulse of one polarity occuring approximately simultaneously with the square wave and a spike of the opposite polarity beginning approximately after the termination of the pulse.

3. An electrical apparatus as recited in claim 2 wherein the pulse and the spike of the output wave are of substantially greater absolute potentials than that potential provided by the regulated potential source means and the battery means.

4. An electrical apparatus as recited in claim 2 wherein each pulse of the output waveform has a width in the range of 60 microseconds, pulse or minus approximately 20%.

5. An electrical apparatus as recited in claim 2 wherein the pulses of the output waveform have a repetition rate in the range of 740 pulses per second, plus or minus approximately 20%.

6. An electrical apparatus as recited in claim 2 further comprising means for providing the pulses of the output waveform at potentials in the range of approximately 200 to 240 volts during the width of the pulse.

7. An electrical apparatus as recited in claim 6 wherein each pulse of the output waveform has width approximately in the range of 60 microseconds, plus or minus 20%.

* * * * *